United States Patent
McNeirney et al.

[11] Patent Number: 5,810,841
[45] Date of Patent: Sep. 22, 1998

[54] ENERGY GUIDED APPARATUS AND METHOD WITH INDICATION OF ALIGNMENT

[75] Inventors: John C. McNeirney, Fairburn, Ga.; Michael K. Landi, Kenmore, N.Y.

[73] Assignee: Minrad Inc., Orchard Park, N.Y.

[21] Appl. No.: 859,380

[22] Filed: May 20, 1997

Related U.S. Application Data

[60] Provisional application No. 60/034,207, Jan. 22, 1997.

[51] Int. Cl.$^6$ .................................................... A61B 19/00
[52] U.S. Cl. ........................... 606/130; 600/424; 33/286; 33/DIG. 21; 356/153
[58] Field of Search .................................... 600/424, 478, 600/114; 604/116, 606, 20, 10, 129, 130; 33/286, DIG. 21; 356/153, 399

[56] References Cited

U.S. PATENT DOCUMENTS

| | | | |
|---|---|---|---|
| 4,012,638 | 3/1977 | Altschuler et al. | 250/491 |
| 4,158,776 | 6/1979 | Barrett | 250/455 T |
| 4,223,227 | 9/1980 | Horwitz | 250/491 |
| 4,651,732 | 3/1987 | Frederick . | |
| 5,031,203 | 7/1991 | Trecha | 378/205 |
| 5,056,129 | 10/1991 | Steinmeyer | 378/705 |
| 5,116,344 | 5/1992 | Sundqvist | 606/130 |
| 5,209,232 | 5/1993 | Levene . | |
| 5,212,720 | 5/1993 | Landi et al. | 378/206 |
| 5,283,808 | 2/1994 | Cramer et al. | 378/206 |
| 5,316,014 | 5/1994 | Livingston . | |
| 5,320,111 | 6/1994 | Livingston . | |
| 5,463,669 | 10/1995 | Kaplan | 378/205 |
| 5,499,989 | 3/1996 | LaBash | 606/130 |
| 5,537,453 | 7/1996 | Williams et al. | 378/206 |
| 5,553,115 | 9/1996 | Odaka et al. | 378/206 |
| 5,572,568 | 11/1996 | Kanemitsu | 378/206 |
| 5,598,269 | 1/1997 | Kitaevich et al. | 606/130 |

*Primary Examiner*—William E. Kamm
*Assistant Examiner*—George R. Evanisko
*Attorney, Agent, or Firm*—Hodgson, Russ, Andrews, Woods & Goodyear, LLP

[57] ABSTRACT

An invasive instrument, such as a biopsy needle, syringe or drill, is adapted to be guided by an energy beam such as a laser beam along a predefined line of sight path toward a subsurface target. The instrument is adapted for use in conjunction with an energy beam targeting and directing system which directs an energy beam in a line of sight path toward a target. The instrument includes a portion for percutaneously accessing a subsurface target, an energy conducting portion and an energy responsive means interposed between the means for percutaneously accessing a subsurface target and the energy conducting portion. In use of the instrument, whereby an operator monitors the energy responsive component for a visual indication of alignment of the instrument with the predefined line of sight path, while advancing the portion for percutaneously accessing the subsurface target along the line of sight path toward the target.

33 Claims, 6 Drawing Sheets

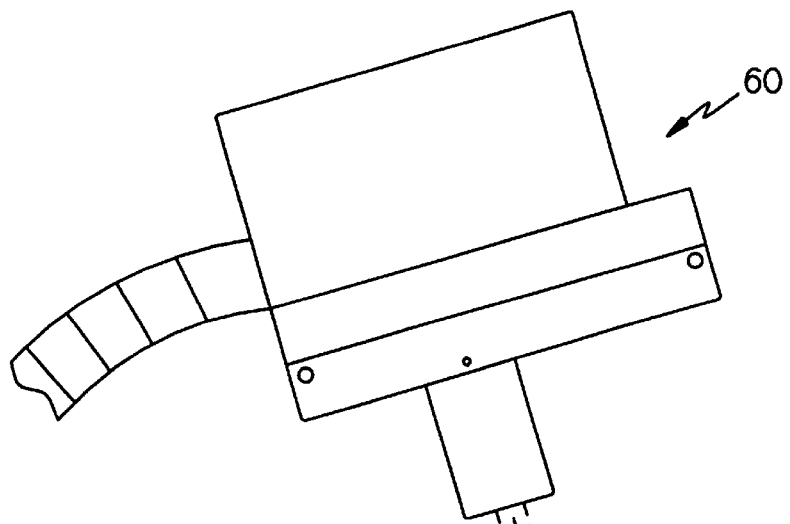
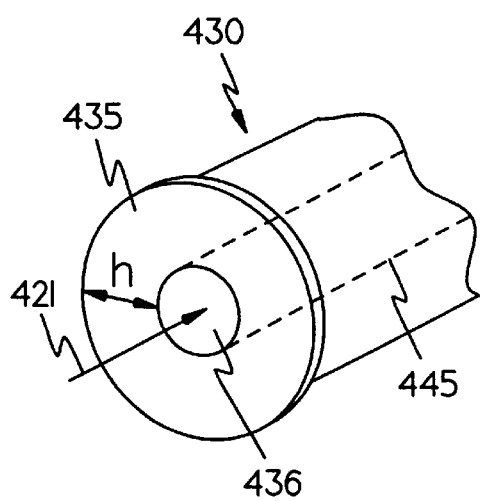
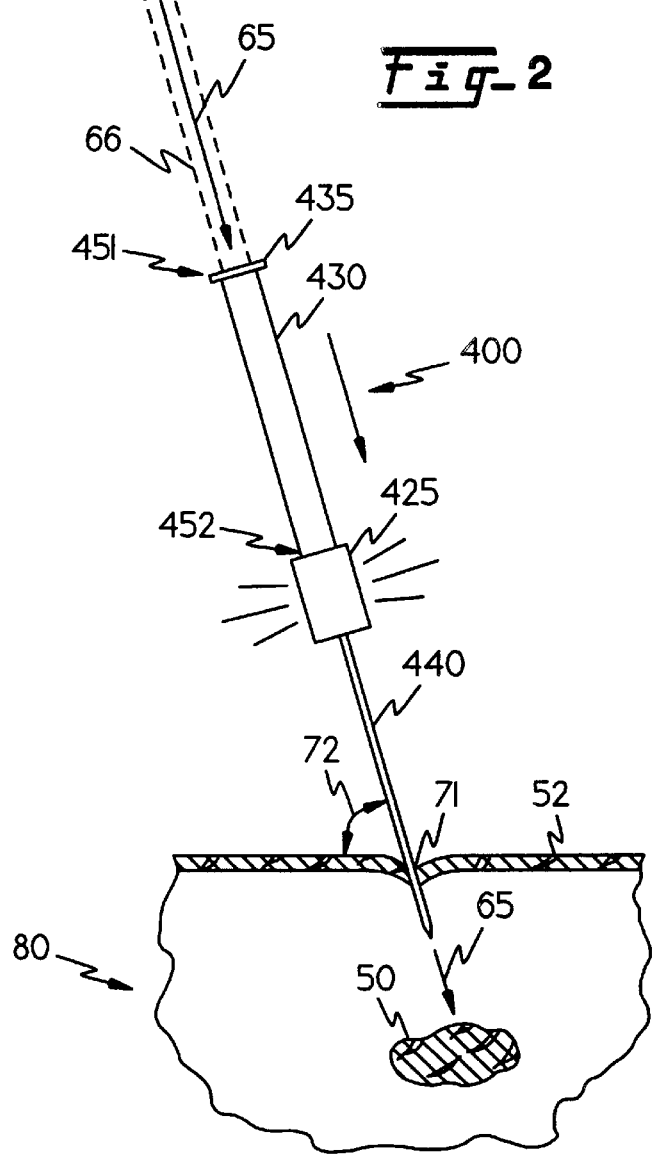
Fig_2
Fig_2A

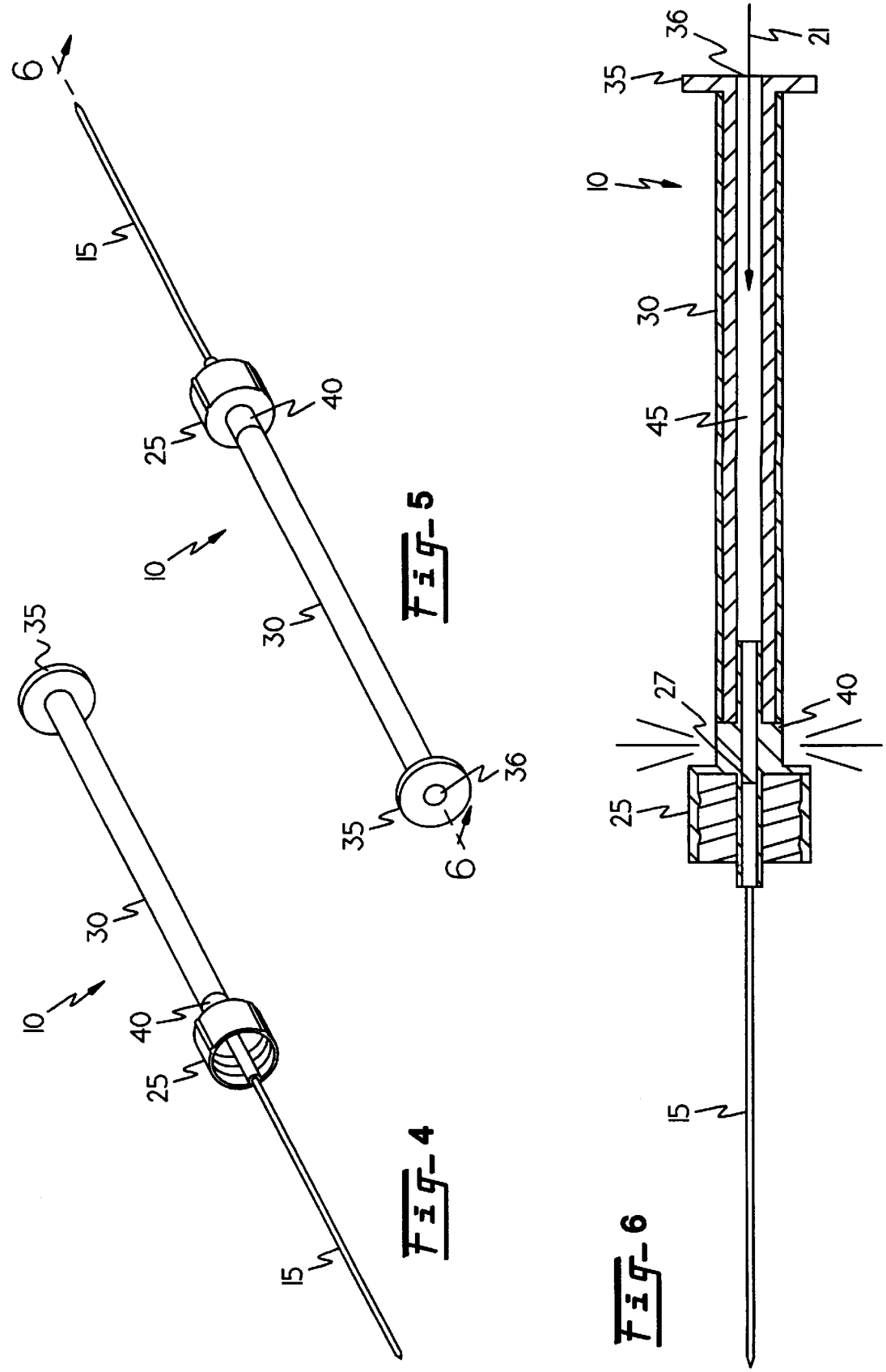

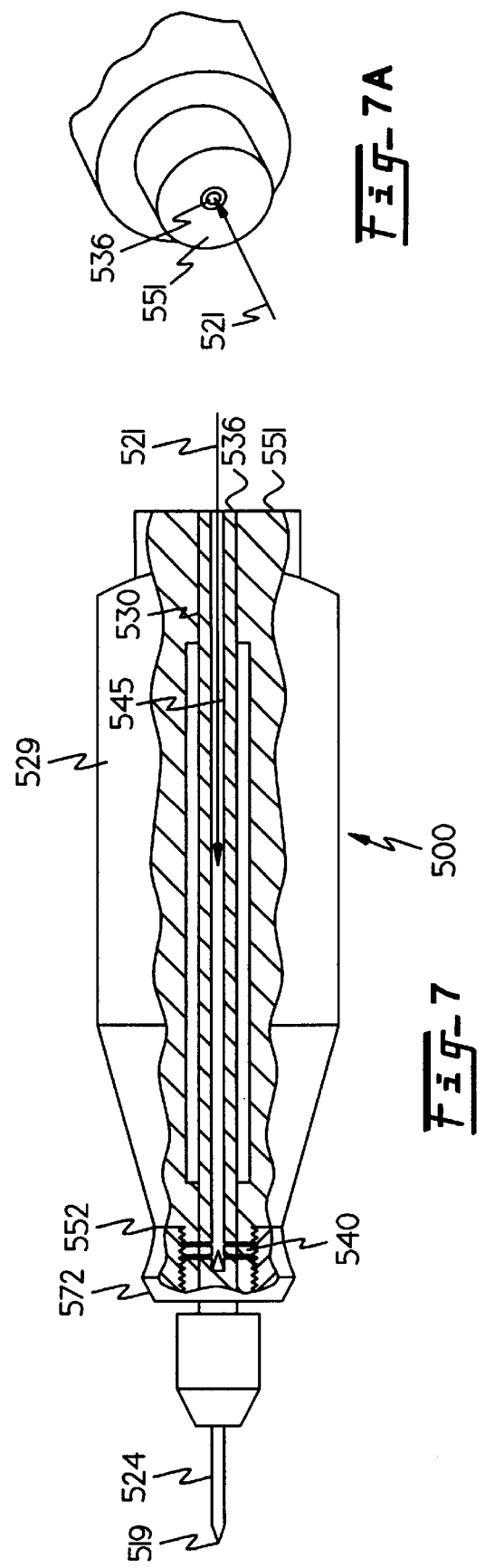

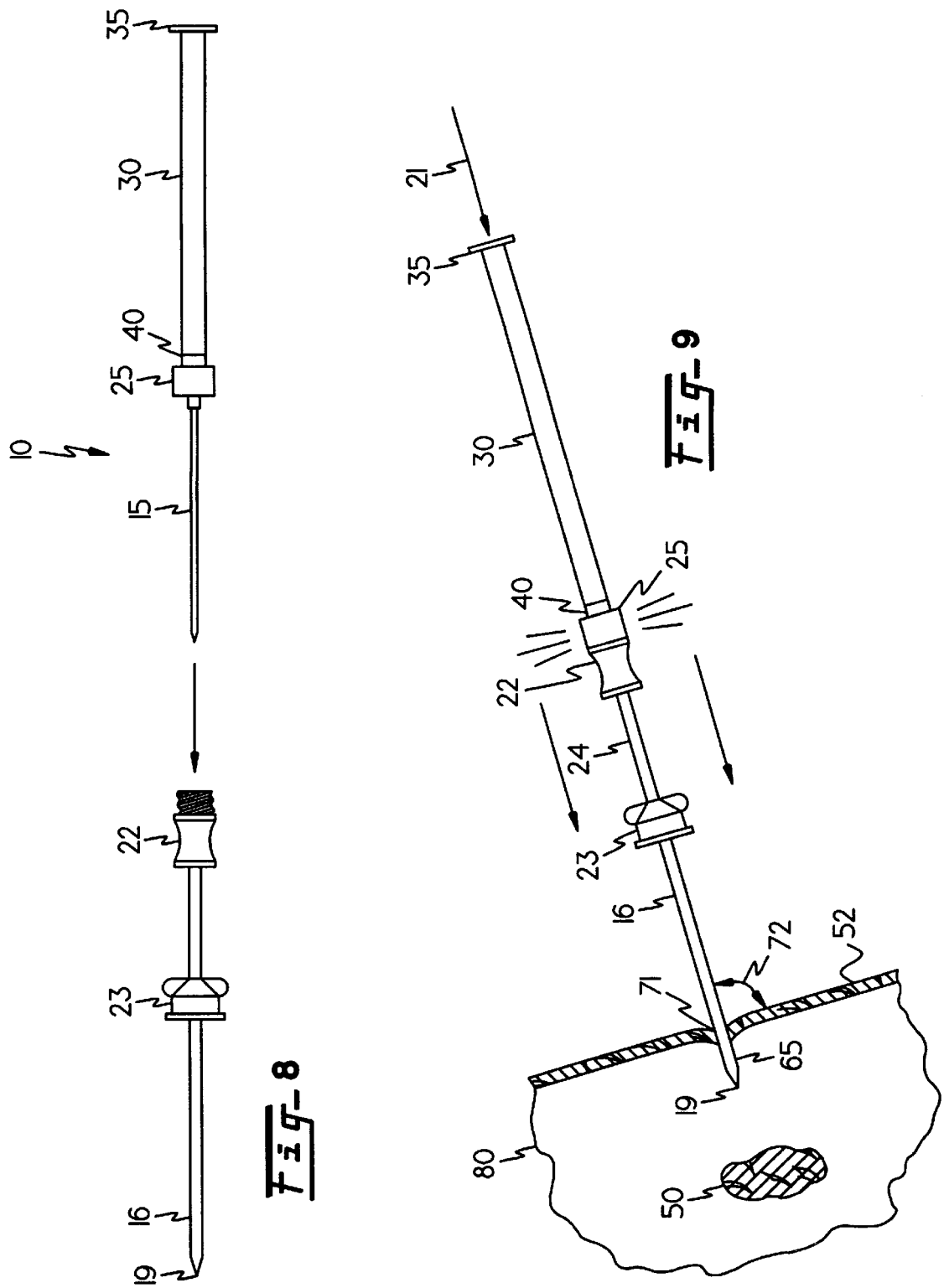

ENERGY GUIDED APPARATUS AND METHOD WITH INDICATION OF ALIGNMENT

CROSS-REFERENCE TO A RELATED APPLICATION

Applicants hereby claim priority on earlier filed provisional application Ser. No. 60/034,207, filed Jan. 22, 1997, which is incorporated herein by reference now abandoned

BACKGROUND OF THE INVENTION

1. Field of the Invention

The present invention relates generally to insertion tools, invasive instruments and the like, and more particularly to an invasive instrument adapted to be guided by an energy beam, such as a visible light beam, to a preselected target within a body, as for example a biopsy needle to a tissue mass within a patient's body.

2. Prior Art

A wide variety of medical procedures, including biopsies, lesion drainage, stereotaxis, and discolysis call for highly accurate placement and insertion of medical instruments such as needles, localization wires or other biopsy tools. Placement and insertion of the instrument at a true access of approach, i.e. a predetermined precise entry point and along a desired line of sight path to a subcutaneous target, during these procedures is of the utmost importance to the success of the procedures.

In many cases CT scans (computerized tomography), or fluoroscopic imaging is performed in conjunction with medical procedures such as biopsies to allow the surgeon to visualize a subsurface, or subcutaneous target, i.e., a portion of the internal anatomy of a patient, such as a tumor, which is medically of interest. The scans provide the surgeon with a cross-sectional image of a patient through a "cut" or "scan" plane which visualizes deep structures such as internal organs, tissues, bony structures and abnormalities. The surgeon uses the images thus obtained to select the optimum line of sight path for the appropriate instrument, whether it is a biopsy needle, drainage catheter or other instrument. The surgeon then guides the instrument along the desired path to the target, or abnormality, to extract or otherwise treat it.

Using available imaging technology, both the insertion depth and angle required for a biopsy needle to align with a desired path to a target can be ascertained with a very high degree of accuracy. In addition, systems are known which are capable of providing selective illumination and sighting to reach specific subsurface members, or targets, of a patient's anatomy. Such a system is disclosed in U.S. Pat. No. 5,212,720 to Landi, et al. (hereby incorporated by reference). In this dual radiation targeting system, subsurface regions of an X-ray transparent but optically opaque object are targeted along a visible line of sight path obtained by the use of two radiation sources, an X-ray and a light beam source, preferably a laser. The laser light beam of this system provides a visible line of sight to the deep structure which is located between the x-ray source and the target. A surgeon may use the visible line of sight to align the invasive instrument along the desired path to the target within the patients body.

In actual practice, however, precise placement and insertion of the instrument with respect to the desired insertion angle, and line of sight path to the target is difficult to maintain. If fluoroscopic imaging alone is used, a trial and error technique is often employed, whereby the surgeon estimates the desired angle of approach, and then slowly advances the needle of the instrument into the patient's body while observing a display to monitor the position of the needle and alter its trajectory as required. This technique has the disadvantage of requiring the surgeon to alternate her or his attention between the instrument and the monitor, which is separated from the instrument.

The resulting inaccuracy of placement can result in significant discomfort to the patient and in some cases requires repeated needle insertions before achieving the proper location of the needle with respect to the target.

In addition, fluoroscopic imaging techniques require repeated fluoroscopic images to obtain position information with concurrent ionizing radiation exposure of both the patient and surgeon. The multiple CT scans tie up available CT scan time, which is highly sought after. Thus it is highly desirable to increase the accuracy of the placement and insertion of the invasive instrument to reduce the length of the procedure, time under anesthesia, and the cumulative ionizing radiation exposure of the patient and the surgeon.

Even when a laser targeting system is employed in conjunction with an imaging system, it is often difficult for the surgeon to monitor and maintain the invasive instrument in alignment with the predetermined line of sight path to the target with a desirable degree of accuracy.

Certain other advancements have been made which offer improvements over the trial and error method for performing CT-based biopsies and other procedures. For example, U.S. Pat. Nos. 4,638,799 and 4,706,665 relate to mechanical guide apparatus for discolysis and stereotactic procedures, respectively. U.S. Pat. No. 4,723,544 discloses another mechanical guide device for discolysis procedures. U.S. Pat. Nos. 4,733,661, 4,930,525 and 5,102,391 relate to guidance devices for CT-guided drainage and biopsy procedures.

Generally, the devices disclosed in the above-referenced patents and publication are rigidly fixed to the CT scanner. Such devices have several drawbacks, however, including the requirement of precise attachment and alignment relative to the CT scanner. Furthermore, the device may obstruct the field of operation of the surgeon, and requires the biopsy procedure to be performed at the location of the CT scanner. Other disclosed devices are separate from the CT scanner, but attach to the ceiling, walls or to the floor. Some devices physically hold the needle or biopsy tool and therefore require sterilization before each use. In addition, some of the above devices provide no means for ensuring accurate placement of the biopsy tool along the desired line of sight path to the target as they relate only to measuring and maintaining the needle insertion angle relative to a longitudinal vertical plane through the patient.

U.S. Pat. No. 4,651,732 to Frederick is based on the principle of two intersecting planes represented by thin sheets of light. The intersection of the planes defines a line which can be positioned to define the correct insertion angle of the biopsy device. In use of this system, the biopsy instrument is held so that during its insertion it casts shadows in both beams of light, thus theoretically assuring that the instrument is following the preselected path of the line defined by the intersection of the two planes.

This system has several disadvantages, however, including the requirement of two separate light sources which must be kept in alignment for the system to work properly. This beam-alignment must be made with an extremely high degree of accuracy since the light sources are positioned a considerable distance from the patient. This system presents the additional difficulty of requiring the surgeon to maintain the biopsy tool in line with the two planes of light simultaneously.

In addition, it is often desirable to non invasively image or "see" the internal structures of animal bodies, as well as the subsurface structures of inanimate objects such as the walls of buildings, bulkheads of ships and the like, when making repairs, or otherwise inserting an invasive instrument such as a drill, bore or punch. Such techniques have also included radiography, fluoroscopy, and more recently ultrasonography, computed tomography and magnetic resonance imaging. However, a need remains for an instrument which can be used in conjunction with imaging and targeting systems to access sub surface targets along a predetermined line of sight path.

Thus, there remains a need for a highly accurate and easy to use invasive instrument which provides an indication of its alignment with a predetermined line of sight path to a target.

SUMMARY OF THE INVENTION

It is therefore an object of the present invention to provide, in a system wherein an energy beam is directed at a preselected target within a body, and wherein an invasive instrument is employed to access the preselected target by penetrating the surface of the body, and wherein the energy beam is incident upon the surface of the body at a desired penetration point, and wherein the direction of the energy beam indicates the desired angle and axis for the invasive instrument to penetrate the body, an invasive instrument including: an elongate energy conducting portion having a distal end and a proximal end, the elongate energy conducting portion adapted to receive the energy beam at the proximal end and to conduct received energy to the distal end. The instrument further includes means for percutaneously accessing the target, and energy responsive means interposed between the means for percutaneously accessing the target and the distal end of the energy conducting portion. The energy responsive means disperses visible light whenever the means for percutaneously accessing the target is in axial alignment with the energy beam.

It is a further object of the invention to provide a combination of an instrument for insertion of a needle into a body and an imaging system adapted to direct an incident beam of light toward a preselected point within the body. The instrument includes an elongate light conducting portion having a distal end and a proximal end, the elongate light conducting portion adapted to receive an incident beam of light at the proximal end and to conduct the incident beam of light to the distal end. The instrument further includes a needle portion collinear and coaxial with the light conducting portion. A light responsive means is interposed between the needle portion and the distal end of the light conducting portion for dispersing visible light whenever the light conducting portion is in axial alignment with the incident beam of light.

It is a further object of the invention to provide a method of providing accurate guidance along a predetermined path of an invasive instrument in invasive procedures in which the instrument is inserted axially into a body. The method comprises the steps of: a) illuminating the predetermined path with a light beam; b)adapting the invasive instrument such that visible light is emitted from the instrument when the instrument is in axial alignment with the illuminated predetermined path; c)aligning the instrument axially with the light beam such that visible light is emitted from the instrument; d) moving the aligned instrument along the predetermined path while maintaining the axial alignment of the instrument with the light beam by monitoring the visible light emitted from the instrument; e)inserting the aligned instrument into the body while maintaining the axial alignment of the instrument with the light beam by monitoring the visible light emitted from the instrument.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore not to be considered limiting of its scope, the invention will be described with additional specificity and detail through use of the accompanying drawings in which:

FIG. 2 is a schematic representation of an invasive instrument according to the present invention as it is used in connection with the energy source of FIG. 1.

FIG. 2A is a perspective view of the proximal end of the energy conducting portion depicted in FIG. 2.

FIG. 4 is a perspective view of a biopsy instrument according to a preferred embodiment of the present invention.

FIG. 5 is a perspective view of the biopsy instrument shown in FIG. 4 viewed from the opposite direction.

FIG. 6 is a side cut away view of the biopsy instrument of FIG. 6.

FIG. 7 is a side view, partially broken away of a drill instrument according to an alternative embodiment of the present invention.

FIG. 7A is a perspective view of the energy conducting portion of the drill instrument shown in FIG. 9.

FIG. 8 is a side elevation view a biopsy instrument according to the present invention showing the cannula of the instrument separated from the stylet.

FIG. 9 is an elevated view of the biopsy instrument as it appears penetrating the surface of a body.

DETAILED DESCRIPTION OF THE PRESENTLY PREFERRED EMBODIMENTS

The following detailed description of the embodiments of the present invention, as represented in FIGS. 1–9, is not intended to limit the scope of the invention, as claimed, but is merely representative of the presently preferred embodiments of the invention. The presently preferred embodiments of the invention will be best understood by reference to the drawings, wherein like parts are designated by like numerals throughout.

Figure 1:
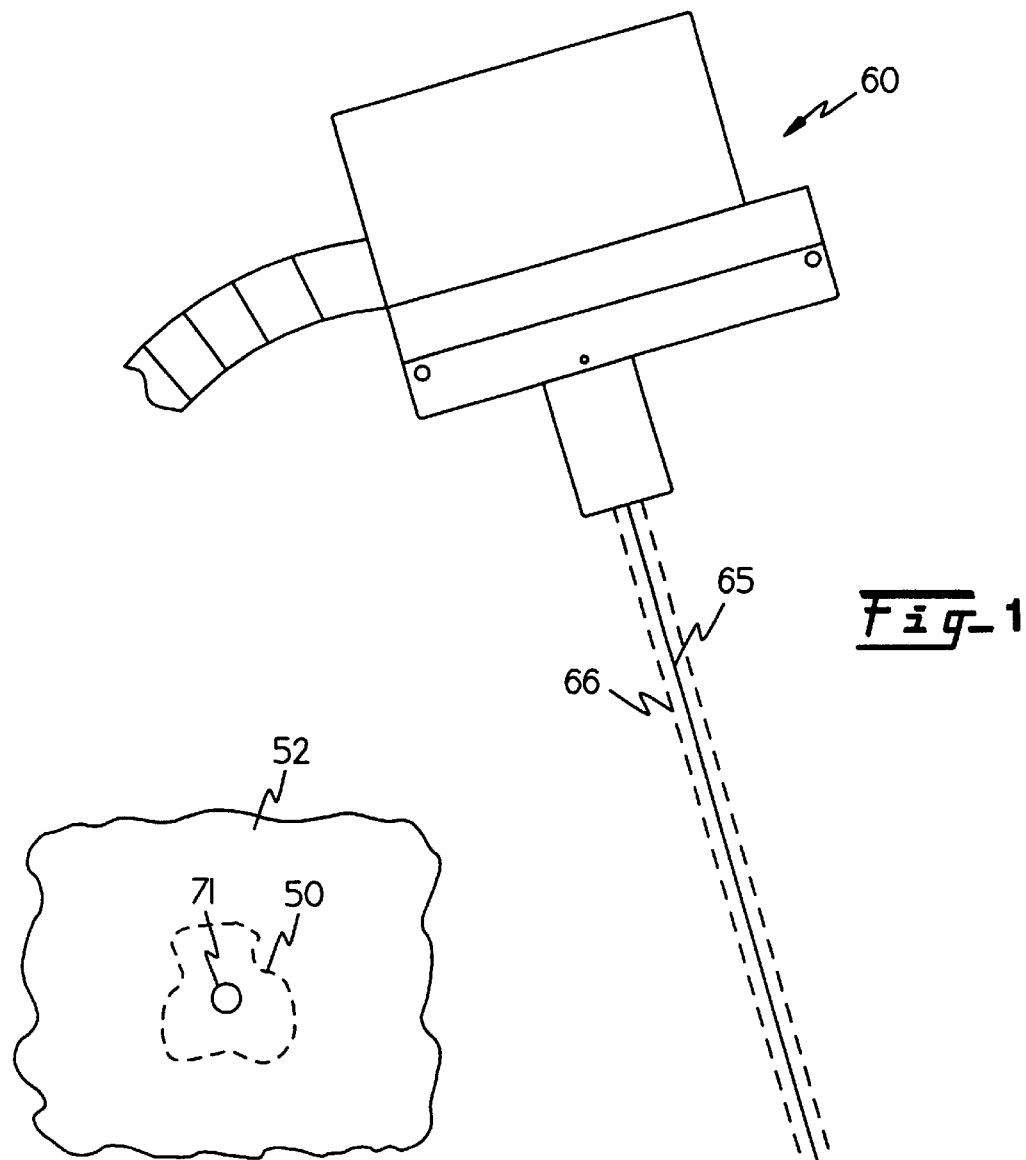
FIG. 1 is a schematic representation of an energy source emitting an energy beam along a predetermined path to a subsurface target as used in connection with the present invention.

Referring now to the drawings, and particularly to FIG. 1, an energy beam targeting system 60, of a type preferred for use in conjunction with the present invention, provides an energy beam 66 which is directed along a predetermined line of sight path 65 toward an imaged subsurface target 50. An imaged subsurface target is a target residing below the surface, or within an object or body, whose location and position within the body is determined through the use of imaging means such as an X-ray system or a CT scanner.

Energy beam 66 is incident on the surface 52, also referred to herein as skin 52, of an object, or body 80 to be penetrated at a point 71, and at an angle 72. Point 71 and angle 72 together help define predetermined line of sight path 65, also referred to as the desired access path 65, to target 50. Energy beam 66, when directed along line of sight path 65 to target 50, can be utilized to guide an invasive instrument (as shown in FIG. 2 at 400) along the path 65 to access a target 50.

Energy beam targeting system 60 is preferably of the dual radiation targeting system type described in U.S. Pat. No. 5,212,720 to Landi et al, hereby incorporated by reference. In this system, subsurface regions of an X-ray transparent, but optically opaque object, such as that shown at 80, are targeted along a visible line of sight path 65, obtained by the use of two radiation sources, an X-ray source and a light beam source 60, preferably a laser.

Once energy beam targeting system 60 has directed energy beam 66 along desired access path 65 to target 50, an invasive instrument such as that shown in FIG. 2 at 400 may be used to penetrate body 80 through skin, or surface 52 thereby percutaneously accessing target 50. The surface 52 can be a patient's body, or a super structure such as a wall, hull or any other surface structure through which it is desired to introduce an invasive instrument in order to access a subsurface target.

FIG. 2 shows invasive instrument 400 according to a preferred embodiment of the present invention. Invasive instrument 400 includes an elongate energy conducting portion 430 having a proximal end 451 and a distal end 452; means 440 for percutaneously accessing target 50, and energy responsive means 425 for dispersing visible light whenever means 440 for percutaneously accessing target 50, and therefore elongate energy conducting portion 430, are in axial alignment with energy beam 66. Means 440 for percutaneously accessing target 50 is preferably collinear and coaxial with elongate energy conducting portion 430.

Energy conducting portion 430 is preferably an elongate rod having a central, coaxial energy conducting channel (as best illustrated in FIG. 2A at 445) extending from proximal end 451 to distal end 452. Energy conducting portion 430 is adapted at proximal end 451 to receive energy beam 66 through opening 436. Opening 436 provides access for an energy beam and allows energy to enter energy conducting channel 445. Opening 436 is preferably surrounded by a flange 435.

Energy conducting channel 445 may be a hollow core, or may comprise any material capable of conducting energy from opening 436 of channel 445 to distal end 452. When the energy is visible light energy, energy conducting channel 445 may be formed of plastic or any other rigid, opaque material capable of conducting the visible light along the length of energy conducting channel 445.

Energy beam 66 is preferably a visible light beam such as a laser beam. In that case flange 435 (best illustrated in FIG. 2A) serves to provide a visual indication of the position of the beam relative to opening 436, allowing the operator, or surgeon, to adjust the position of invasive instrument 400 such that energy beam 66 enters opening 436 in alignment with the axis 421 of energy conducting channel 445. The width h of flange 35 may vary according to desired indication. A narrow flange width h results in less visual contact with energy beam 466, when the axis of invasive instrument 400 is out of alignment with energy beam 66. A wider flange width results in visual contact with energy beam 66 over a wider deviation in alignment. Flange 435 is preferably white, or light in color such that the energy beam 66 forms a more focused and clear visible spot on the surface of flange 435 upon incidence.

As will be appreciated by those skilled in the art, a wide variety of instruments and tools having various means for percutaneously accessing a target similar to that shown in FIG. 2 at 440, may be adapted to include energy conducting portion 430, energy conducting channel 445, and energy responsive means 425. In addition to medical instruments, these instruments include drills, bores, punches and any other implement used to penetrate a surface to reach a subsurface target.

As those skilled in the electronics arts will appreciate, an energy beam may comprise visible light, such as infra red light, or the light provided by a laser, or other forms of energy capable of being transmitted in the form of a directed beam, such as cathode rays, electron beams and the like. Energy responsive means 425 may be a translucent or other material responsive to visible light, or may be a sensor responsive to electromagnetic transmissions of other types. Energy responsive means 425 may provide a visual indication in response to the energy it receives, or it may provide an audible or tactile indication in response to the received energy. All of these variations are intended to remain within the scope of the present invention.

FIG. 3 illustrates general design principles to be considered when constructing energy conducting portion 430. As can be seen from the drawings, and according to well known principles, the relationship between length l of energy conducting portion 430 and the diameter d of energy conducting channel 445 determine the maximum deviation e from either side of central axis 21 which can be tolerated, still allowing energy beam 66 to traverse the length l of energy conducting portion 430.

An energy conducting portion 430 having a given diameter d (such as that shown in FIG. 3A), and a given length l, determine the allowable deviation e from axis 21, before energy beam 66 will be prevented from traversing channel and reaching energy responsive means 425. If the allowable deviation e is exceeded, energy responsive means 425 will not illuminate. The failure to illuminate signals an out of alignment condition of instrument 400 with path 65.

Figure 3A:
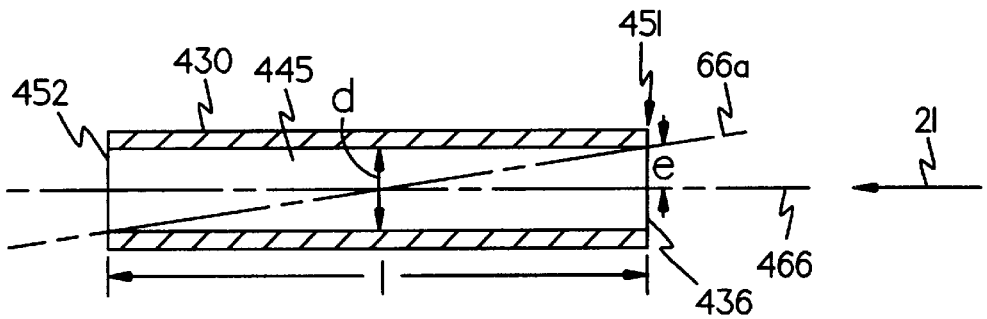
FIG. 3A depicts the relationship between the length l and the diameter d of the energy conducting portion of the present invention.
Figure 3B:
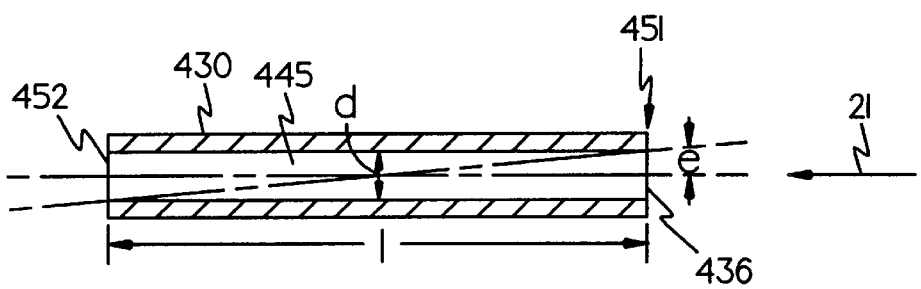
FIG. 3B depicts the relationship between the length l and the diameter d of the energy conducting portion of the present invention when d is decreased.

An energy conducting portion 430 having the same length l as shown in FIG. 3A at l, but a lesser diameter d (as shown in FIG. 3B), will tolerate less deviation e from axis 21 before energy responsive means 425 extinguishes.

Figure 3C:
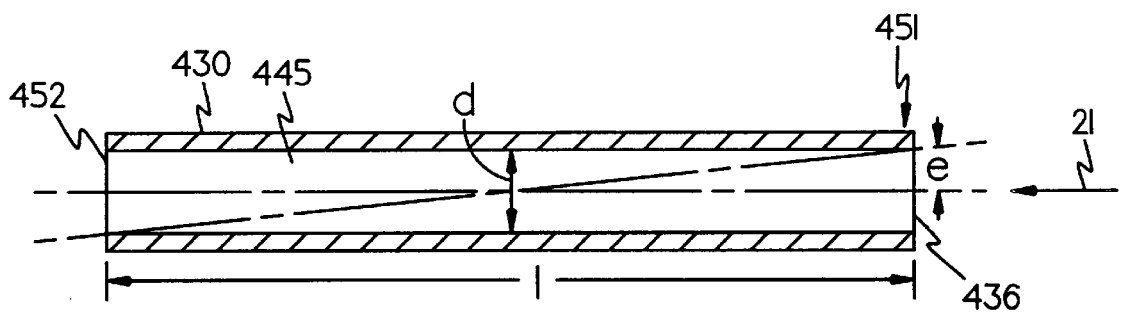
FIG. 3C depicts the relationship between the length l and the diameter d of the energy conducting portion of the present invention when l is increased.

FIG. 3C illustrates the effect of a longer length l of energy conducting portion 430 for a given diameter d. A longer length l results in less tolerance for deviation e from axis 21 and greater accuracy and alignment capability for instrument 400.

Turning now to FIGS. 4, 5 and 6, there is shown an invasive instrument according to the principles of the present invention as embodied in a biopsy instrument 10, a preferred embodiment. Biopsy instrument 10 is adapted to be responsive to light energy in the form of a laser beam as best illustrated in FIG. 1 at 66.

In the embodiment shown at 10, an elongate energy conducting portion comprises a casing 30, having an energy conducting channel 45 disposed therewithin. Casing 30 may be constructed of plastic or other suitable materials having energy responsive properties which will allow a directed light beam, such as a laser beam, to travel in a generally straight line path along the axis of casing 30 from proximal end 51 to distal end 52. In addition, casing 30 provides a convenient gripping surface whereby biopsy instrument 10 may be firmly grasped by the operator during insertion.

Energy conducting channel 45 may comprise a hollow cylindrical inner core of casing 30, which core is adapted to receive a directed laser beam at an opening 36 located at the proximal end of casing 30, and to conduct the laser beam in a generally straight line path therethrough, from the proximal end of casing 30 to the distal end. If desired, the interior surface of casing 30 which so forms energy conducting channel 45 may be provided with suitable light responsive, or reflective coatings which maximize the light conducting properties of energy conducting channel 45 according to principles well known in the optical arts.

Alternatively, energy conducting channel 45 may readily comprise any suitable light conducting, or translucent material, as opposed to comprising a hollow core. Suitable materials are those which allow light from the laser beam to pass from the proximal end of casing 30 to the distal end only when the laser beam is in coaxial alignment with axis 21 of channel 45 within the desired tolerance (+/−e, as discussed in connection with FIGS. 3A, 3B and 3C).

In accordance with the principals of the present invention, biopsy instrument 10 further includes means for percutaneously accessing a target, in this case a needle (best illustrated in FIG. 9 at 24) comprised of a stylet means 15, a puncturing cannula means 16 (shown in FIGS. 8, and 9) and cannula mount means 22 (shown in FIGS. 10, and 11). Stylet means 15 is telescopically or coaxially received within the cannula mount means 22 to assemble needle 24.

The energy responsive element of biopsy instrument 10 comprises a portion 40 of a connecting hub means 25. Connecting hub means 25 and energy dispersing element 40 may be a Luer™ Lock, having a light transparent portion, as commonly used in the medical arts. Connecting hub means 25 is interposed between casing 30 and needle 24 by affixing hub means 25 to the distal end of casing 30 by conventional means well known in the art. The end 27 of stylet means 15 serves to block passage of light from the laser beam past energy responsive means 40, thereby causing light energy to be substantially dispersed through the translucent material from which energy responsive means 40 is constructed The dispersed light energy causes energy responsive means 40 to illuminate when the laser beam reaches the distal end of energy conducting channel 45.

In a preferred embodiment of biopsy instrument 10, the length l of casing 30 is 10 cm and the inner diameter d is 2 mm. Energy responsive means 40 has an outer diameter of 6.5 mm and is 7.0 mm in length However, these dimensions are not restrictive and a wide latitude in the dimensions of instrument 10 is permissible while allowing the instrument to function as described herein.

Biopsy instrument 10 will now be described as it would be implemented in conjunction with the energy beam directing system illustrated in FIGS. 1 and 1A. A laser beam targeting system 60 such as the one described in U.S. Pat. No. 5,212,720 to Landi, et al, is used to direct a laser beam 66 along a line of sight path 65 to a subsurface target 50 within a patient's body 80. The laser beam 66 creates a visible spot 71 on the desired entry site on the patient's skin 52. The laser beam 66 also illuminates the line of sight path 65, which, if followed, would lead to the target 50 beneath the patient's skin 52. With this arrangement, the precise angle 72 necessary for the biopsy instrument shown in FIGS. 4, 5, 6, 8, and 9 at 10, to reach its target 50 as defined by the laser beam 72 may be determined as well.

The operator, or surgeon, places the tip 19 of needle 16 of biopsy instrument 10 on the visible spot 71 (best shown in FIG. 1A) and aligns casing 30 with the illuminated line of site path 65 (shown in FIG. 1) such that casing 30 is in approximate axial alignment with the laser beam. That is, light from the beam enters opening 36. The location of the laser beam relative to opening 36 may be determined by the operator simply by visual observation of the relative positions of opening 36 and the laser beam.

The visual observation described above may be aided by flange 35 which surrounds opening 36. When the laser beam is incident upon the surface of flange 35 it creates a visible spot of light which may be visually monitored by the operator as the operator adjusts the angular position of biopsy instrument 10, and thereby the alignment of casing 30 with the laser beam. The operator may adjust the angular position of biopsy instrument 10 until the laser beam appears to be aligned with opening 36.

When casing 30 is in angular alignment with the laser beam energy responsive means 40 will illuminate, i.e., disperse visible light. The operator monitors the illumination of energy responsive means 40 as s/he percutaneously accesses target 50, i.e., penetrates the surface 52, in this case the skin of the patient, and inserts needle 16 into the body of the patient until needle 16 is in contact with target 50. As the operator advances needle 16 toward target 50, s/he observes energy responsive means 40, adjusting the position of energy conducting portion 30 so as to maintain illumination of energy responsive means 40 as indicated by the dispersion of visible light therefrom. Accordingly, the desired path to target area 50 is maintained as the operator advances the biopsy instrument toward target 50.

As those skilled in the art will appreciate based on the foregoing description, a variety of invasive instruments having needles such as fluid aspiration needles (such as amniocentesis needles) and other needles may be adapted for use in this invention. Also the instrument 10 of the present invention may be adapted for use in various biopsy techniques, including cytologic aspiration, fluid aspiration, histological biopsies, as well as coaxial percutaneous biopsy techniques.

Furthermore the present invention may be adapted for use with medical instruments other than just needles wherever improved guidance mechanisms are desired. For example, trocars, insertable scopes, catheters and the like may be provided with an energy responsive element, responsive to a beam of directed visible light directed along a path to a target.

FIG. 7 illustrates yet another invasive instrument, a drill instrument 500, adapted in accordance with the principles of the present invention. An energy conducting portion is provided by adapting shaft 530 of drill instrument 500 to include an energy conducting channel 545 having an opening 536 at proximal end 551. In the drill instrument 500 of this embodiment, the shaft 530 is the energy conducting portion of the invasive drill instrument 500.

Energy conducting channel 545 preferably extends from opening 536 to distal end 553 of shaft 530 of drill body 529, such that the central longitudinal axis 521 of energy conducting channel 545 is in coaxial and collinear alignment with the axis of means for percutaneously accessing a target, in the case a drill bit 524.

Yoke portion 572 of drill instrument 500 is adapted to include an energy responsive means 540, which is interposed between drill bit 524 and elongate energy conducting portion 530. Energy responsive means 540 can be a translucent ring, or collar which is positioned to surround distal end 552 of energy conducting channel 545 such that light from channel 545 may be dispersed through energy responsive means 540 so as to be visible to an operator when light reaches distal end 552.

Figure 1A:
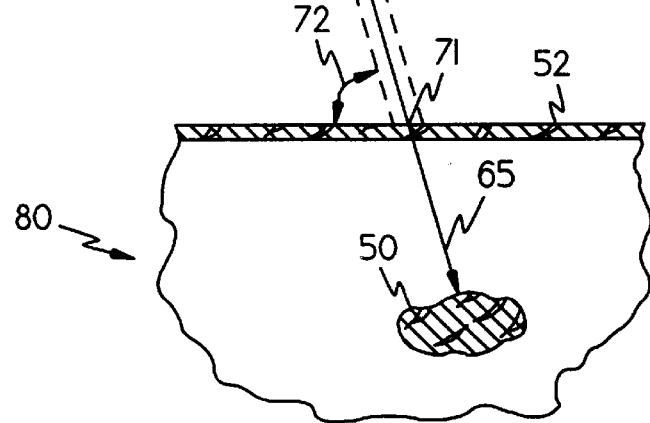
FIG. 1A is a top view of the surface to be penetrated.

In operation, a laser targeting and positioning system 60 as previously described and illustrated in FIGS. 1 and 1A, is used to direct a laser beam 66 at a subsurface target area 50. The operator positions the tip 519 of the drill bit 524 (shown in FIG. 7) on the spot 71 created by the incidence of the laser beam 66 on the surface 52 to be penetrated, as described above in connection with alternative embodiments.

When shaft 530 is in angular alignment with the laser beam along axis 521, energy responsive means 540 will illuminate, i.e., disperse visible light. The operator monitors the illumination of energy responsive means 540 as s/he percutaneously accesses target 50, i.e., by penetrating the surface 52 of body 80 with drill bit 524 until drill bit 524 reaches the desired target area 50. As the operator advances drill bit 524 toward target area 50, s/he observes energy responsive means 540, adjusting the position of energy conducting portion 530 so as to maintain illumination of energy responsive means 540, as indicated by the dispersion of visible light therefrom. Accordingly, the desired path to target area 50 is maintained.

What is claimed is:

1. In a system comprising means for directing an energy beam at a preselected target within a body and wherein an invasive instrument is employed to access the preselected target by penetrating the surface of the body, and wherein the energy beam is incident upon the surface of the body at a desired penetration point, and wherein the direction of the energy beam indicates the desired angle and axis for the invasive instrument to penetrate the body, an the invasive instrument comprising:
   an elongate energy conducting portion having a distal end and a proximal end, said elongate energy conducting portion adapted to receive the energy beam at said proximal end and to conduct the energy beam to said distal end;
   means for percutaneously accessing the target; and
   energy responsive means interposed between said means for percutaneously accessing the target and said distal end of said energy conducting portion, said energy responsive means serving to disperse visible light whenever said means for percutaneously accessing the target is in axial alignment with the energy beam.

2. The invasive instrument of claim 1 wherein said means for percutaneously accessing the target is collinear and co-axial with said elongate energy conducting portion.

3. The invasive instrument of claim 1 wherein the energy beam comprises a visible light beam, and wherein said elongate energy conducting portion is provided with an energy conducting channel to conduct said visible light beam, and wherein said energy responsive means is responsive to said visible light beam.

4. The invasive instrument of claim 3 wherein said visible light is a laser.

5. The invasive instrument of claim 1 wherein the invasive instrument is a biopsy instrument and said means for percutaneously accessing the target is a biopsy needle coupled to said biopsy instrument.

6. The invasive instrument of claim 1 wherein the invasive instrument is a syringe and said means for percutaneously accessing the target is a needle coupled to said syringe.

7. The invasive instrument of claim 1 wherein the invasive instrument is a drill and said means for percutaneously accessing the target is a drill bit.

8. The invasive instrument of claim 1 wherein said means for percutaneously accessing the target is a needle.

9. The invasive instrument of claim 1 wherein said means for percutaneously accessing the target is a puncturing cannula.

10. The invasive instrument of claim 1 wherein said means for percutaneously accessing the target is a drill bit.

11. The invasive instrument of claim 1 wherein said means for percutaneously accessing the target is a boring means.

12. The invasive instrument of claim 1 wherein said elongate light conducting portion is a hollow, opaque cylinder.

13. An instrument for insertion of a needle into a body for use with an imaging system having means for directing a light beam at a preselected target within the body and an instrument having an entry point of the light beam, the instrument comprising:
   an elongate light conducting portion having a distal end and a proximal end, said elongate light conducting portion adapted to receive the incident beam of light at said proximal end and to conduct the incident beam of light to said distal end;
   a needle portion collinear and coaxial with said elongate light conducting portion; and
   light responsive means interposed between said needle portion and said distal end of said elongate light conducting portion for dispersing the light beam whenever said elongate light conducting portion is in axial alignment with the light beam.

14. The combination of claim 13 wherein said instrument is a biopsy needle.

15. The combination of claim 14 wherein said biopsy needle includes a puncturing cannula and a stylet.

16. A method of monitoring the alignment of an instrument with a visible light beam, the method comprising the steps of:
   a) providing a visible light beam;
   b) providing an instrument having an elongate light conducting portion, said elongate light conducting portion having a distal end and a proximal end and adapted to receive the visible light beam at said proximal end and to conduct received light from said proximal end to said distal end; a penetrating portion collinear and coaxial with said light conducting portion; light dispersing means interposed between said penetrating portion and said distal end of said light conducting portion for dispersing visible light whenever the penetrating portion is in axial alignment with the visible light beam;
   c) monitoring said light dispersing means;
   d) adjusting the position of said instrument with respect to said visible light beam such that said light dispersing means disperses visible light.

17. The method of claim 16 wherein the monitoring step is accomplished by a human.

18. The method of claim 16 wherein the monitoring step is performed by electronic means.

19. The method of claim 16 including the further step of maintaining the position of said instrument with respect to said visible light beam such that visible light is continuously dispersed from said light dispersing element.

20. A device for penetrating a subsurface target along a predetermined path and at a predetermined penetration angle, the device comprising:

means for penetrating a surface located at one end of said device;

an elongate energy conducting portion located at the other end of said device and coupled to said penetrating means;

means for dispersing visible light interposed between said elongate energy conducting portion and said means for penetrating a surface;

said elongate energy conducting portion adapted to include a linearly extending energy conducting channel extending from the proximal end of said elongate energy conducting portion and terminating within said means for dispersing visible light, said linearly extending energy conducting channel being coaxial and collinear with said means for penetrating a surface.

21. The device of claim 20 wherein said means for penetrating is a needle.

22. The device of claim 20 wherein said means for penetrating is a drill bit.

23. The device of claim 20 wherein said elongate energy conducting portion includes means for driving said penetrating means toward the subsurface target.

24. The device of claim 23 wherein said means for driving is a drill motor.

25. The device of claim 20 wherein said elongate energy conducting portion is a handle and said linearly extending energy conducting channel is a cylindrical opening disposed within and extending from the proximal end of said handle to said means for dispersing visible light.

26. The device of claim 20 wherein said light dispersing means is a connecting hub.

27. The device of claim 26 wherein said connecting hub is fabricated from a clear plastic material.

28. A method of providing accurate guidance along a predetermined path of an invasive instrument in invasive procedures in which the instrument is inserted axially into a body, the method comprising the steps of:

illuminating the predetermined path with a light beam;

aligning the instrument axially with the light beam such that visible light is emitted from the instrument;

causing the light beam to enter the invasive instrument such that visible light is emitted from a sensing means carried by the instrument when the instrument is in axial alignment with the illuminated predetermined path;

moving the aligned instrument along the predetermined path while maintaining the axial alignment of the instrument with the light beam by monitoring the visible light emitted from the instrument; and inserting the aligned instrument into the body while maintaining the axial alignment of the instrument with the light beam by monitoring the visible light emitted from the instrument.

29. In a system comprising means for directing an energy beam at a preselected target within a body and wherein an invasive instrument is employed to access the preselected target by penetrating the surface of the body, and wherein the energy beam is incident upon the surface of the body at a desired penetration point, and wherein the direction of the energy beam indicates the desired angle and axis for the invasive instrument to penetrate the body, the invasive instrument comprising:

an elongate energy conducting portion having a distal end and a proximal end, said elongate energy conducting portion adapted to receive the energy beam at said proximal end and to conduct the energy beam to said distal end;

means for percutaneously accessing the target; and energy responsive means interposed between said means for percutaneously accessing the target and said distal end of said energy conducting portion, said energy responsive means indicating proper alignment of the energy beam to said means for percutaneously accessing the target.

30. A method of aligning a light beam and an invasive instrument in a system comprising means for providing a light beam, the invasive instrument having a sensing means carried by the invasive instrument and an entry point for the light beam, the method comprising the steps of:

providing the light beam;

positioning the invasive instrument in a manner such that the light beam travels into the invasive instrument through the point of entry; and observing the response of the sensing means, the response being indicative of either alignment or misalignment of the light beam to the invasive instrument.

31. The method of claim 30 further comprising the step of adjusting the position of the invasive instrument so that the sensing means indicates the proper alignment of the light beam to the invasive instrument when misalignment was indicated during the step of observing response of the sensing means.

32. An invasive instrument adapted for alignment with a light beam, the invasive instrument comprising:

an invasive instrument body having a point of entry for the light beam;

a sensing means carried by the invasive instrument body, the sensing means being spaced from the point of entry of the light beam and providing an indication of either alignment or misalignment of the light beam to the invasive instrument; and a conducting means associated with the invasive instrument body for directing the light beam from the point of entry to the sensing means.

33. The invasive instrument according to claim 32, wherein the conducting means comprises an elongate light conducting channel within the instrument body.

\* \* \* \* \*

UNITED STATES PATENT AND TRADEMARK OFFICE
CERTIFICATE OF CORRECTION

PATENT NO.  : 5,810,841
DATED       : September 22, 1998
INVENTOR(S) : John C. McNeirney et al It is certified that error appears in the above-indentified patent and that said Letters Patent is hereby corrected as shown below:

Col. 6, lines 21 and 22 delete "infra red light, or"

Col. 10, line 37 change "combination" to --instrument--.

Col. 10, line 39 - change "combination" to --instrument--.

Signed and Sealed this

Eleventh Day of May, 1999

Attest:

Attesting Officer

Q. TODD DICKINSON

Acting Commissioner of Patents and Trademarks